United States Patent [19]

Wampler

[11] Patent Number: 5,061,256
[45] Date of Patent: Oct. 29, 1991

[54] INFLOW CANNULA FOR INTRAVASCULAR BLOOD PUMPS

[75] Inventor: Richard K. Wampler, Gold River, Calif.

[73] Assignee: Johnson & Johnson, New Brunswick, N.J.

[21] Appl. No.: 385,558

[22] Filed: Jul. 26, 1989

Related U.S. Application Data

[63] Continuation-in-part of Ser. No. 129,713, Dec. 7, 1987, abandoned.

[51] Int. Cl.$^5$ .......................... A61M 5/00; A61F 1/24
[52] U.S. Cl. .................................. 604/280; 604/264; 600/16
[58] Field of Search ................ 128/656, 658; 600/16–18; 604/53, 96, 151, 264, 280, 281, 282; 623/3

[56] References Cited

U.S. PATENT DOCUMENTS

| | | | |
|---|---|---|---|
| 3,435,826 | 4/1969 | Fogarty | 606/194 |
| 3,995,617 | 12/1976 | Watkivos et al. | 600/16 |
| 4,033,331 | 7/1977 | Guss et al. | 604/281 |
| 4,508,535 | 4/1985 | Joh et al. | 604/282 |
| 4,527,549 | 7/1985 | Gabbay | 600/18 |
| 4,625,712 | 12/1986 | Wampler | 604/264 |
| 4,639,252 | 1/1987 | Kelly et al. | 604/282 |
| 4,737,153 | 4/1988 | Shimamura et al. | 604/282 |
| 4,747,840 | 5/1988 | Ladika et al. | 604/264 |
| 4,748,984 | 6/1988 | Patel | 604/284 |
| 4,777,951 | 10/1988 | Cribier et al. | 604/96 |

FOREIGN PATENT DOCUMENTS

| | | | |
|---|---|---|---|
| 823320 | 12/1951 | Fed. Rep. of Germany | 604/282 |
| 2568777 | 2/1986 | France | 604/264 |

OTHER PUBLICATIONS

USCU Sales Brochure 6–74/5070107.

*Primary Examiner*—Stephen C. Pellegrino
*Assistant Examiner*—Ralph A. Lewis
*Attorney, Agent, or Firm*—Weissenberger, Peterson, Uxa & Myers

[57] ABSTRACT

An inflow cannula for intraortic blood pumps has a curved, spring-loaded body for blind retrograde insertion through the aortic arch, and a soft, beveled foldable but resilient tip which properly positions the tip, if necessary, with respect to the aortic valve prior to retrograde insertion of the distal end of the cannula through the aortic valve. Auxiliary intake openings are provided in the side walls of the cannula adjacent its distal end to prevent suction from holding the tip in its collapsed state after insertion through the aortic valve.

3 Claims, 5 Drawing Sheets

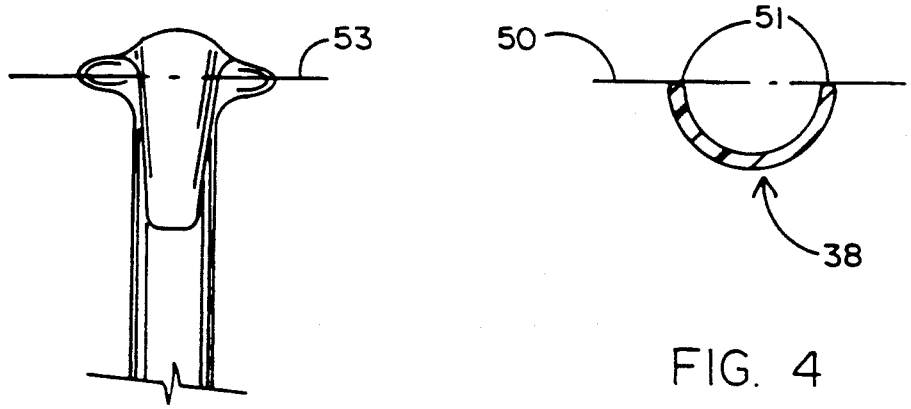
FIG. 5
FIG. 4
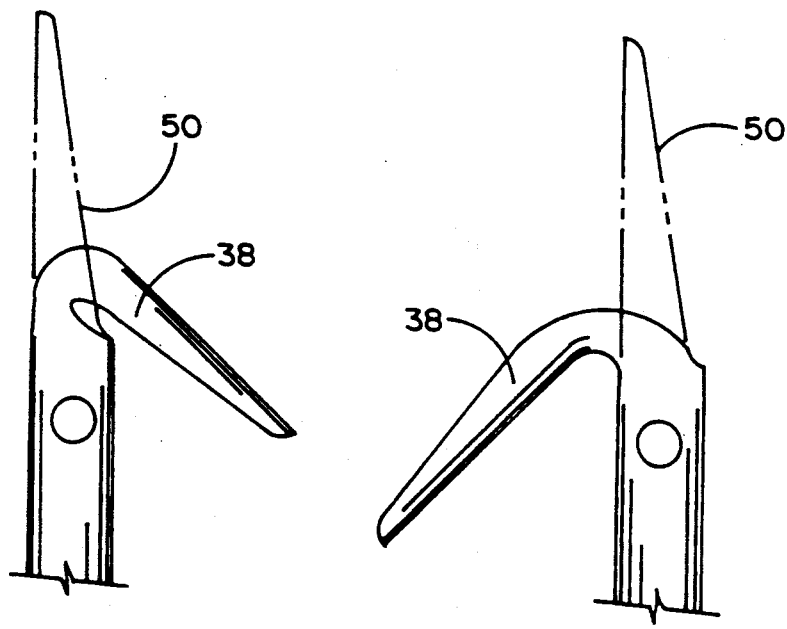
FIG. 6
FIG. 7

INFLOW CANNULA FOR INTRAVASCULAR BLOOD PUMPS

STATEMENT OF RELATED CASES

This application is a continuation-in-part of application Ser. No. 129,713 filed Dec. 7, 1987 and also entitled "Inflow Cannula For Intravascular Blood Pumps" now abandoned.

FIELD OF THE INVENTION

This invention relates to an inflow cannula for blind insertion of an intravascular blood pump, and more particularly to a cannula with a beveled tip which pushes the cannula to the center of the aortic valve for retrograde traversal.

BACKGROUND OF THE INVENTION

U.S. Pat. No. 4,625,712 and copending application Ser. No. 129,714 filed 12/07/87 disclose miniature high-speed blood pumps which can be threaded through a blood vessel to provide heart assist in emergency situations without major surgery. Typically, such pumps are inserted through, e.g., the femoral artery. An inflow cannula is positioned ahead of the pump during insertion, and this cannula must typically be pushed through the aortic valve in a retrograde direction.

In the past, such retrograde insertion was usually done by means of a wire guide over which the inflow cannula was slipped, and which was subsequently withdrawn. This method was unsatisfactory not only because it was awkward and carried a risk of injury to the vascular system and to the aortic valve, but also because it required the continuing observation of the wire during insertion by x-ray or other procedures. In an emergency, appropriate x-ray equipment may not be immediately available, and heart assist may have to be provided so quickly that the slow wire guide method may not be suitable.

A requirement therefore exists for an inflow cannula which can be attached to the intake of an intravascular blood pump and can be pushed ahead of the pump for blind retrograde insertion into the left ventricle through the aortic valve without any additional apparatus and without danger of injury to the patient.

SUMMARY OF THE INVENTION

The present invention fulfills this requirement by providing a wire-reinforced silicon rubber cannula which has a spring-loaded curve built into it. This curve allows a reliable traverse of the aortic arch without getting the cannula caught in a major vessel such as, e.g., the left subclavian artery. The cannula of this invention carries at its leading end a soft, beveled tip which is so positioned with respect to the built-in curve that the tip tends to point inwardly of the curve.

The softness of the tip material and the elongated bevel of the tip, which forms a pair of elongated shoulders of increasing depth extending transversely of the cannula axis between the distal and proximal ends of the tip, combine to make the tip bend near the proximal end of the beveled section, backward or forward, in a direction generally normal to the plane of the bevel, when it presses against an obstacle.

As the tip approaches the aortic valve, one of two things occur: if the tip is centered with respect to the aortic valve, and the valve is open (as during systole) as the tip is pushed through it, the tip passes through the aortic valve without deformation. If, however, the valve is closed (as during diastole), or if the tip is substantially off center, its distal end may slide into a sinus of the aortic valve.

When this happens, the distal end of the tip, due to the beveled shape of the tip, folds forward or backward upon itself about a line generally in the bevel plane. In so doing, it tends to push the body of the cannula toward the center of the valve annulus. Due to the bowl shape of the sinuses, the tip end tends to slide toward their center, and the folding of the tip end tends to position the distal end of the cannula over a commisure of the aortic valve, where it can easily penetrate without injury to the sinuses.

As a practical matter, the physician may move and twist the cannula back and forth if it appears that the flexible tip is catching in a sinus. Successful penetration at a commisure or in the center of the annulus occurs easily due to the spring action of the cannula (which was longitudinally compressed by pushing against the sinus) as soon as a valve leaflet is pushed aside or the valve opens on systole.

After the cannula has entered the left ventricle, the flexible tip springs back to its original shape and allows blood to flow into the cannula without obstruction. Apertures are provided in the side of the cannula adjacent its distal end to prevent occlusion of the cannula intake by the flexible tip as a result of the pump's suction.

The considerable softness of the tip prevents irritation of the ventricle (e.g. tickling which can cause arrythmia, fibrillations, or premature ventricular contractions); yet the tip is stiff enough to bend or fold neatly without rolling or telescoping. The flat shape of the distal end of the tip prevents it from entering the coronary ostia if it slides into the sinuses.

It is therefore the object of this invention to provide an inflow cannula for intravascular blood pumps which is suitable for blind retrograde insertion into the left ventricle of the heart through the aortic valve without substantial risk of injury.

It is another object of the invention to accomplish this purpose by using a cannula with a spring-loaded curve and a soft, flexible tip which is beveled toward the inside of the curve and is capable of temporarily folding upon itself upon encountering the aortic valve so as to center the cannula for penetration through the aortic valve.

BRIEF DESCRIPTION OF THE DRAWINGS

FIG. 4 is a transverse section of the distal tip of the cannula along line 4—4 of FIG. 3;

FIG. 5 is a front elevation of the distal tip of the cannula of FIG. 3 in its forwardly folded position;

FIG. 6 is a side elevation of the tip in the position of FIG. 5;

FIG. 7 is a side elevation corresponding to FIG. 6 but showing the tip in the rearwardly folded position.

DESCRIPTION OF THE PREFERRED EMBODIMENT

Figure 1:
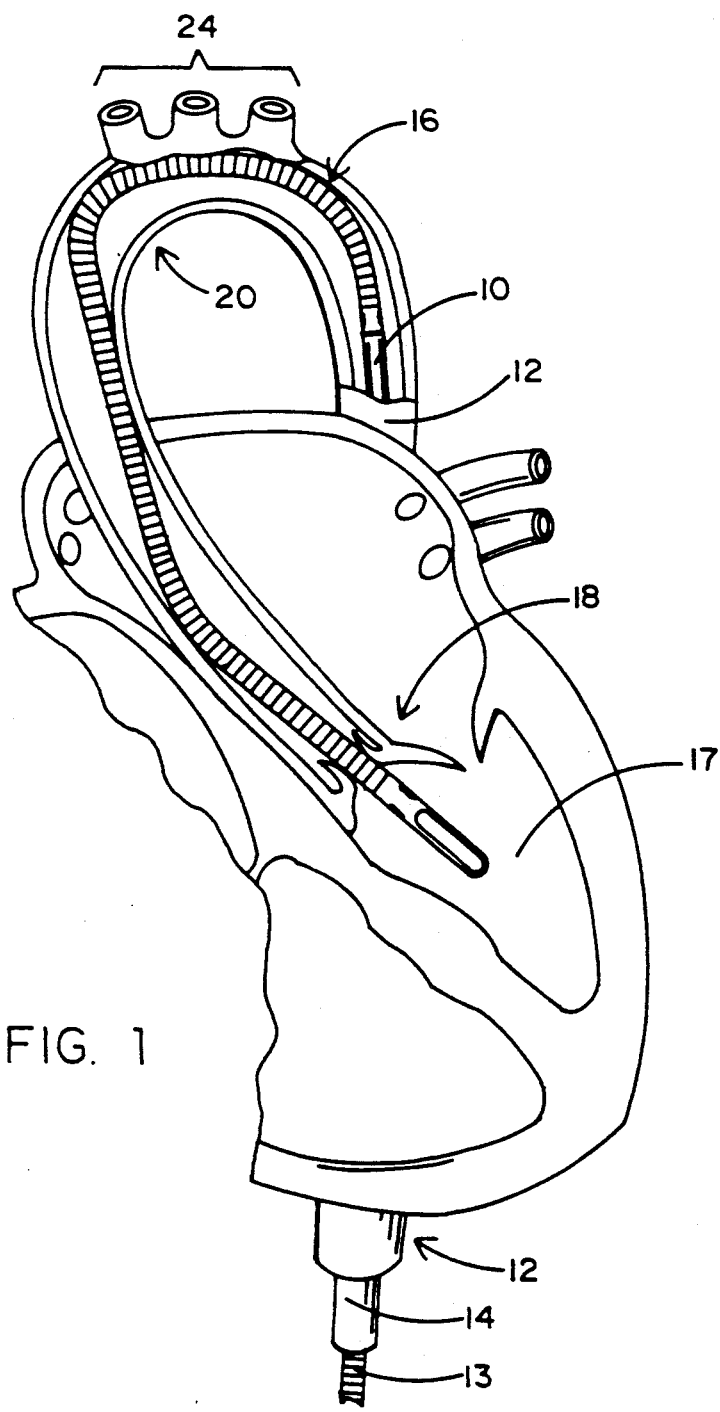
FIG. 1 is a schematic view illustrating the use of the invention in the arterial system of a patient.

FIG. 1 shows, in schematic form, the environment in which the invention is used. When heart assist is needed in an emergency or for other medical reasons, a miniature intravascular blood pump 10 is percutaneously inserted into the femoral artery (not shown) and is pushed through the femoral artery into the aorta 12. Rotary power for the cable drive 13 of pump 10 and purge fluid for its hydrostatic bearings is supplied through a catheter 14 from outside the patient's body, as described in more detail in copending application Ser. No. 129,714 filed 12/07/87. The cannula 16 of this invention is attached to the distal (i.e. intake) end of the pump 10 and guides it through the patient's arterial system during insertion.

In order to assure a steady blood flow through the pump 10, it is desirable to locate the blood intake in the left ventricle 17 of the heart; i.e. the distal end of the inflow cannula 16 must be passed through the aortic valve 18. This poses several problems, particularly in emergency situations where no x-ray equipment is readily available to track the insertion of the cannula 16. To begin with, the cannula 16 must follow the aortic arch 20 smoothly without getting caught in one of the major arteries 24 branching off from the aorta 12 in the arch 20. Next, the cannula 16 must be substantially centered in the aorta 13 as it approaches the aortic valve 18 so as not to get caught in or injure the sinuses 28 (FIG. 11) while penetrating through the valve 18 or pushing aside the aortic leaflets 30. Finally, once the cannula 16 has passed through the aortic valve 18, its inflow opening must be completely unobstructed. All of these procedures must, of course, be accomplished with minimal risk of injury to the patient's vascular system. In addition, once the cannula is in place in the heart, it must not irritate or tickle the ventricle wall for fear of producing arrythmia, fibrillations, or premature ventricular contractions, or mechanical endocardial injury.

Figure 3:
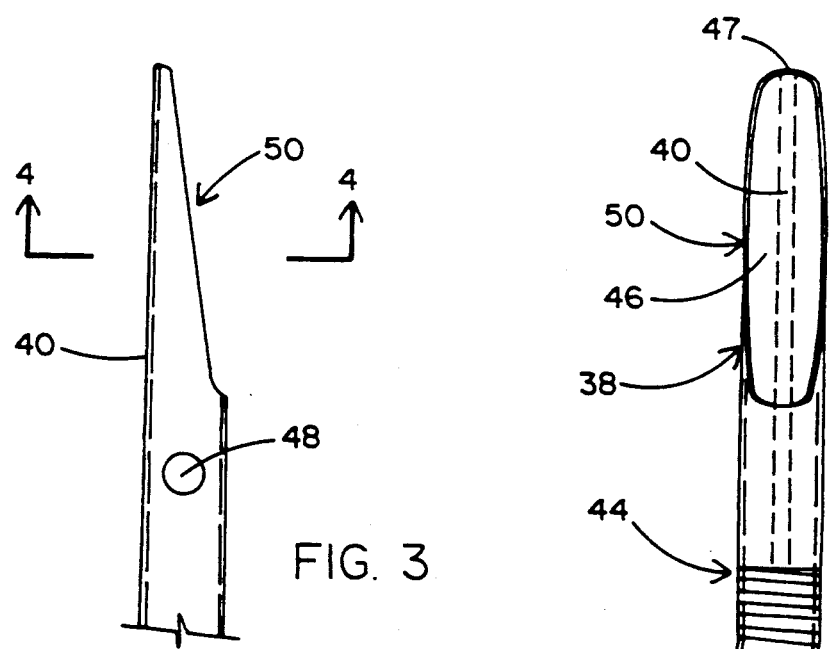
FIG. 3 is a side elevation of the tip of the cannula of FIG. 2.
Figure 2:
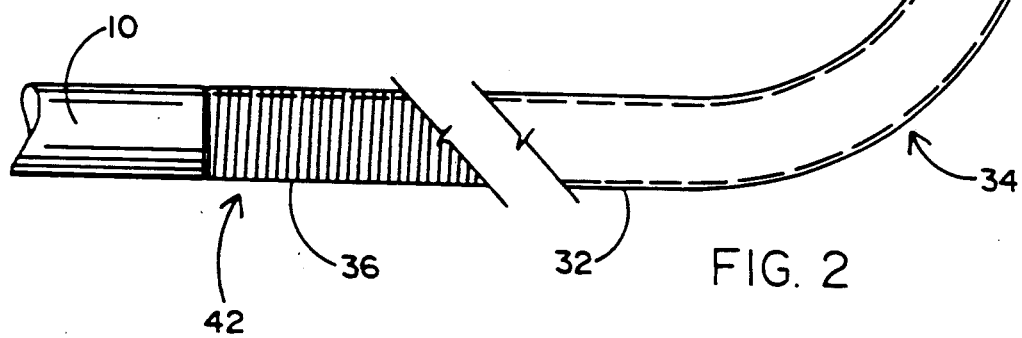
FIG. 2 is a plan view of the cannula of this invention.
Figure 8:
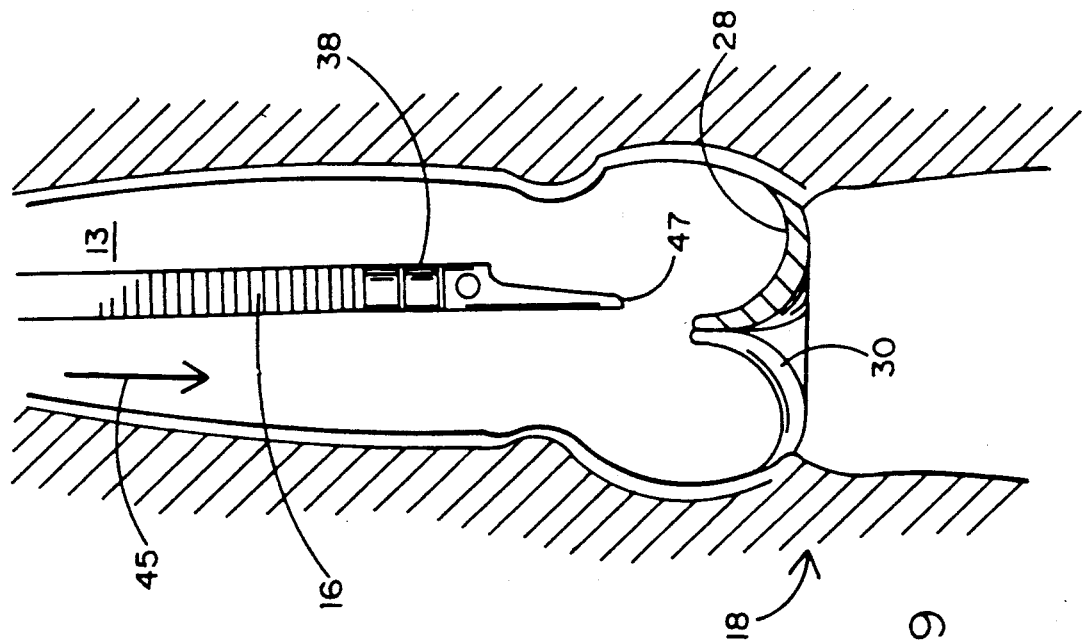
FIG. 8 is a vertical section of the arotic valve showing passage of the cannula during systole.
Figure 9:
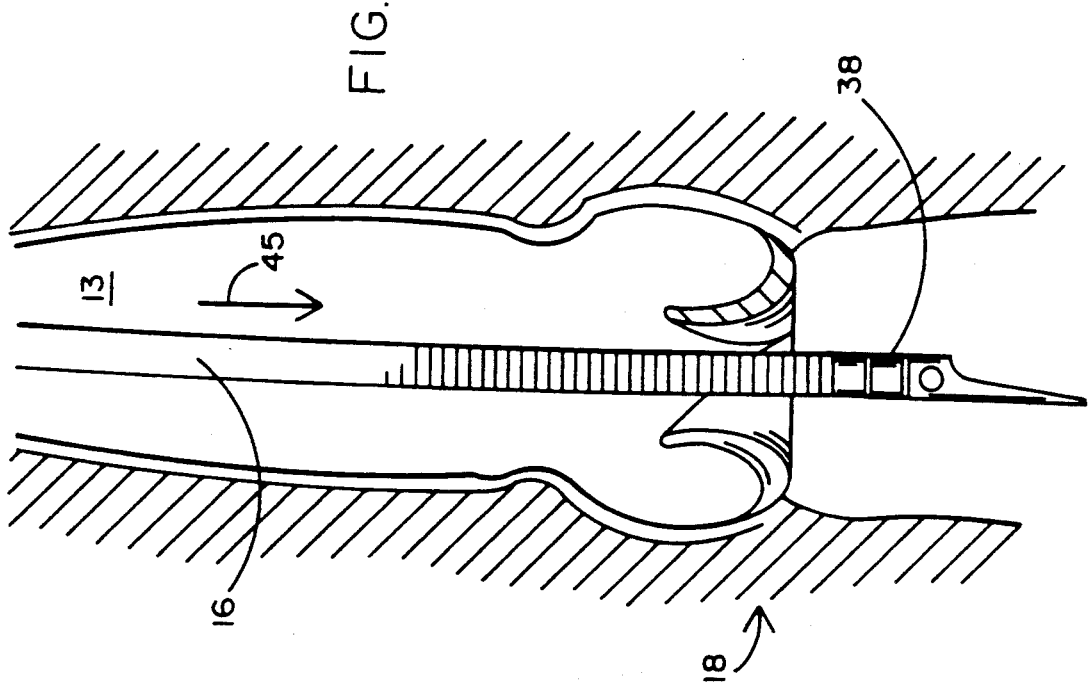
FIG. 9 is a vertical section of the aortic valve showing an off-center approach of the cannula during diastole.

FIGS. 2 and 3 show the inventive cannula structure which fulfills these requirements. The cannula 16 is formed from a tube 32 of soft silicon rubber which, in its body section 34, covers a spring 36. The tip section 38 of the cannula 16 beyond the distal end of spring 36 is beveled for a purpose described below. A radioopaque strip 40 may be interposed between the tube 32 and the spring 36, and extended to the distal end of the tip section 38, for x-ray tracking of the cannula insertion when x-ray equipment is available.

In accordance with one aspect of the invention, conventional forming techniques are employed to bias the body section 34 of cannula 16 into the arcuate shape best illustrated in FIG. 2. This bias urges the cannula 16 to follow the curve of the aortic arch 20 upon insertion and keeps it away from the branch arteries while it traverses the aortic arch. Of course, the loading imposed by spring 36 is weak enough to allow the body section 34 to be straightened by the walls of the arteries when it traverses a straight section of artery.

On each end of its arcuate portion, the body section 34 has short straight portions 42,44. The proximal straight portion 42 may be attached to the intake end of pump 10 in any conventional manner, and the distal straight portion 44 allows the intake opening 46 to remain centered in the left ventricle 17 (FIG. 1) after traversing the aortic valve 18. As a general indication of the parameters of the cannula 16, its diameter may be on the order of 7 mm; the arcuate portion of the body section 34 may have a radius on the order of 2.5 cm; the straight portion 42 may be on the order of 10 cm long; and the straight portion 44 may have a length on the order of 4 mm, not counting the 4 cm-long tip section 38. As best shown in FIG. 3, the tip section 38 is beveled at its distal end along a bevel plane 50 lying at about a 20° angle to the tip's axis. A pair of auxiliary openings 48 are provided in the side of tip section 38, and the distal end 47 of the tip section 38 is cut off flat as best shown in FIG. 2, for purposes discussed below.

Figure 11:
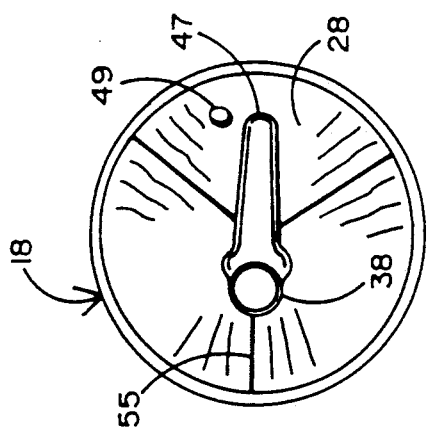
FIG. 11 is a plan view of the aortic valve along line 11—11 of FIG. 10.

FIGS. 8 through 12 show in more detail what happens as the tip section 38 contacts the aortic valve 18 when moving in the direction of arrow 45. If the aortic valve 18 is open (as during systole, FIG. 8) and the tip 38 is reasonably centered as it approaches the valve 18, it passes through the valve 18 unaltered. If, however, the valve 18 is closed (as during diastole, FIG. 9), or if the tip 38 approaches it substantially off center, the flat distal extremity 47 (FIG. 2) of tip 38 contacts one of the aortic leaflets 30 and slides down its side into the sinus 28. If the sinus 28 is one into which a coronary ostium opens, the flat shape and width of the tip extremity 47 prevents the tip 38 from entering the ostium 49 (FIG. 11).

The beveling of the tip 38 along plane 50 results in the formation of shoulders 51 (FIG. 4) between the distal and proximal ends of tip section 38. When the soft tip lodges in a sinus 28, the shoulders 51 cause the distal end of tip section 38 to fold over the proximal end along a line 53 (FIG. 5) lying in the bevel plane 50 in a direction perpendicular to the plane 50. Depending upon which sinus 28 the tip 38 contacts, it may fold forward (FIG. 6) or backward (FIG. 7). In either event, the folding movement of tip 38 in the sinus 28 (FIG. 10) pushes the proximal end of tip 38 over a commisure 55 (FIG. 11) where the cannula 16 can penetrate the aortic valve 18 most easily and without risk of injury to the leaflets 30 or sinuses 28.

It is consequently essential that the material of tip 38 be soft enough to fold readily and to avoid irritating the heart's ventricular walls, yet be strong enough to fold rather than roll or telescope upon encountering an obstruction such as a sinus 28.

Figure 12:
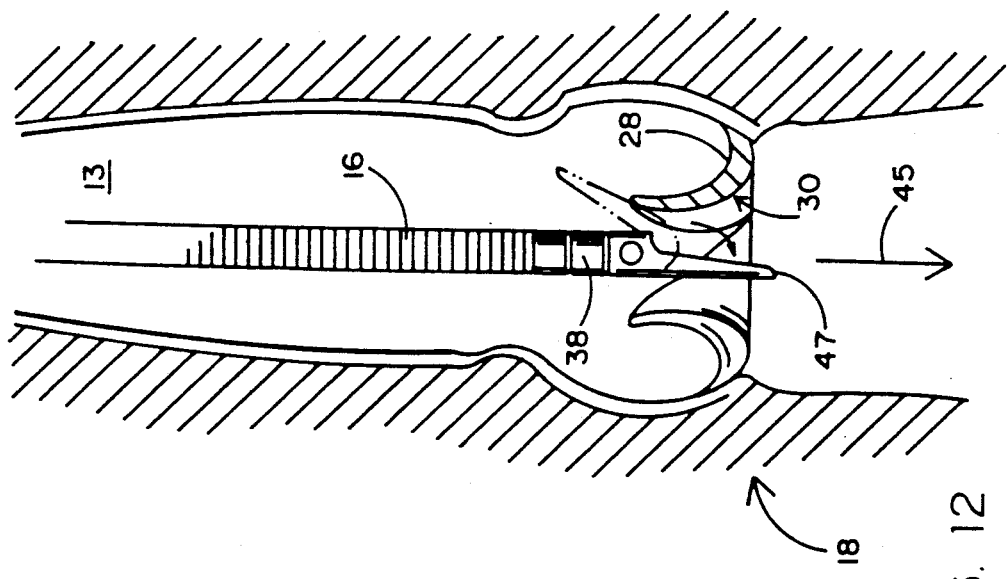
FIG. 12 is a vertical section of the aortic valve showing penetration of the cannula following the condition of FIG. 10.
Figure 10:
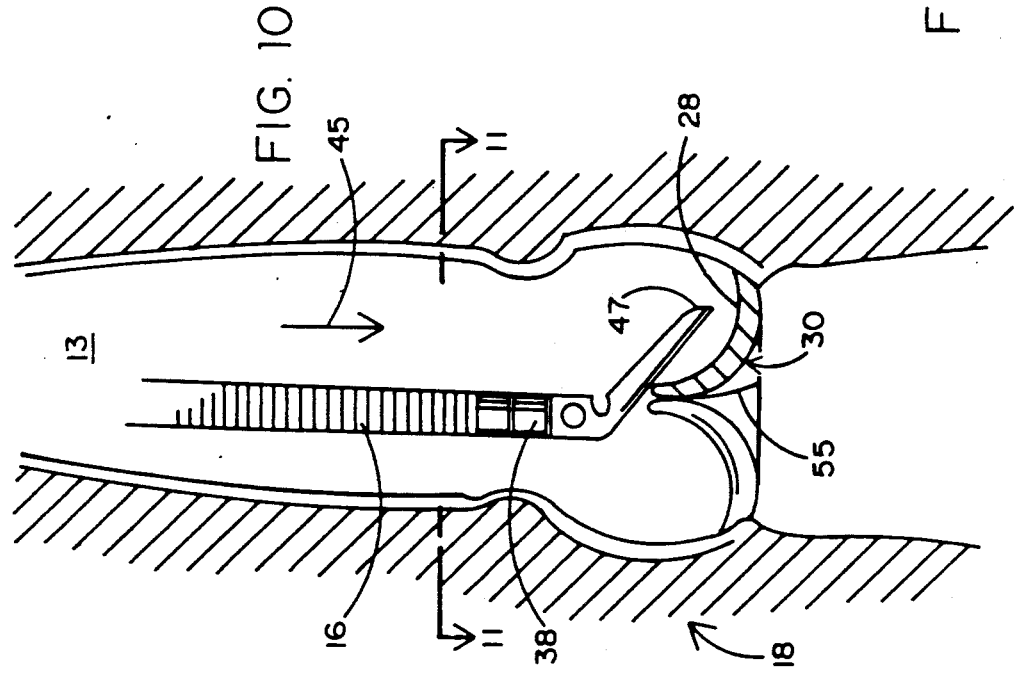
FIG. 10 is a vertical section of the arotic valve showing entry of the cannula tip into a sinus during diastole.

As the body section 34 of cannula 16 traverses the aortic valve 18 after a folding motion of tip 38, the distal end of tip 38 folds over the intake opening 46 of cannula 16 and follows the leading end of the body section 34 into the left ventricle 17. As soon as the folded portion of tip 38 has passed entirely through the aortic valve 18, its resiliency causes it to spring back to its original shape where it leaves the intake opening 46 unobstructed (FIG. 12).

It is possible that the suction of pump 10 may hold the folded distal end of tip 38 against the intake opening 46 and prevent it from returning to its original shape. To avoid this problem, auxiliary openings 48 are provided in the side of the tip section 38. The auxiliary openings 48 provide a sufficient bypass flow path to allow the inherent resilience of the tip section 38 to overcome any suction force at the intake opening 46, even if the pump 10 is operating at maximum speed.

As illustrated in FIG. 3, the auxiliary openings 48 are preferably so positioned that their axes are parallel to the bevel plane 50. In this manner, the folded portion of tip 38 (which, as pointed out above, can only fold in a direction perpendicular to the bevel plane 50) is prevented from obstructing either of the auxiliary openings 48 during passage of the tip 38 through the aortic valve 18.

It will be seen that the present invention provides an inflow cannula for intravascular pumps which is suitable for rapid, blind retrograde insertion into the left ventricle of a human heart when immediate heart assist is called for in emergencies or other situations.

I claim:

1. An inflow cannula for retrograde insertion of the blood intake for an intravascular blood pump through the aortic valve, comprising:

(a) a substantially stiff body section adapted to be attached at is proximal end to the intake of an intravascular blood pump; and (b) a substantially soft, elongated, flexible resilient tip section at the distal end of said body section;

(c) the distal end portion of said tip section being beveled and being sufficiently soft to fold upon itself when pushed into a sinus of said aortic valve;

(d) said beveled distal end portion being so shaped that it folds upon itself only in a direction normal to the plane of the bevel; and (e) which said body section includes an arcuate portion biased into a shape approximating the curvature of a human aortic arch, said distal end being beveled toward the inside of said curvature.

2. The cannula of claim 1, in which portions biased into a straight shape are provided in said body section on each end of said arcuate portion.

3. The cannula of claim 2, in which said bias is a spring bias.

* * * * *